United States Patent [19]
McGarry et al.

[11] Patent Number: 6,126,591
[45] Date of Patent: Oct. 3, 2000

[54] VIDEO ENDOSCOPE FOR USE WITH A FLEXIBLE VIDEO MONITOR ASSEMBLY, A VIDEO MONITOR MOUNT FOR MOUNTING A VIDEO MONITOR TO A VIDEO ENDOSCOPE OR A MOUNTING POST, AND A KIT INCLUDING A FLEXIBLE VIDEO MONITOR ASSEMBLY, A VIDEO ENDOSCOPE AND A MOUNTING POST

[76] Inventors: Eugene McGarry, 49 Lawrence St., Greenlawn, N.Y. 11740; Anthony Martin, 21401 Birdhollow Dr., Trabuco Canyon, Calif. 92679

[21] Appl. No.: 09/053,306

[22] Filed: Apr. 1, 1998

[51] Int. Cl.⁷ .................................................. A61B 1/04
[52] U.S. Cl. ...................... 600/102; 600/109; 600/160; 600/101
[58] Field of Search .................... 600/101, 102, 600/109, 111, 113, 114, 131, 160

[56] References Cited

U.S. PATENT DOCUMENTS

| | | | |
|---|---|---|---|
| 4,610,242 | 9/1986 | Santangelo et al. | 600/114 |
| 5,373,317 | 12/1994 | Salvati et al. . | |
| 5,441,042 | 8/1995 | Putman | 600/102 |
| 5,647,838 | 7/1997 | Bloomer | 600/111 |
| 5,840,013 | 11/1998 | Lee et al. | 600/114 |
| 5,873,814 | 2/1999 | Adair | 600/109 |

OTHER PUBLICATIONS

"Palmcorder Camcorders", (11 HTML pages downloaded from http://www.panasonic.com/PCEC/palmcorder.html on Aug. 5, 1997).

Product brochure entitled: "Remote Visual Inspection (RVI) Systems", *Olympus Industrial*, p. 19, with front and rear covers (Jul. 1996).

Product brochure entitled: "Remote Visual Inspection (RVI) for the Airlines", *Olympus Industrial*, p. 9, with front and rear covers.

*Primary Examiner*—John P. Leubecker
*Attorney, Agent, or Firm*—Straub & Pokotylo; John C. Pokotylo

[57] ABSTRACT

A remote visual inspection system having a video endoscope, a mounting post and a mount. The mount, to which a video monitor is attached, can also accommodate, at any one time, either the video endoscope or the mounting post. The video endoscope has an insertion tube and a scope body. The mount includes a sleeve which defines a central opening into which the scope body and mounting post may extend and has a slot, extending from a first end of the sleeve to a second end of the sleeve, through which the insertion tube may pass. The scope body is provided with a first part (e.g., a pin hole) of a locking mechanism and a first part (e.g., an alignment projection) of an alignment mechanism. The mounting post also has a first part (e.g., a pin hole) of the locking mechanism and a first part (e.g., an alignment projection) of the alignment mechanism. Complementary portions of the locking and alignment mechanisms are located on the sleeve. When the scope body is properly inserted and positioned in the sleeve, the corresponding portions of the locking and alignment mechanisms engage to align and lock the axial and rotational position of the scope body with respect to the mount. The locking and alignment mechanisms between the post and the sleeve similarly engage when the post is properly inserted and positioned in the sleeve to align and lock the position of the post with respect to the mount.

38 Claims, 8 Drawing Sheets

VIDEO ENDOSCOPE FOR USE WITH A FLEXIBLE VIDEO MONITOR ASSEMBLY, A VIDEO MONITOR MOUNT FOR MOUNTING A VIDEO MONITOR TO A VIDEO ENDOSCOPE OR A MOUNTING POST, AND A KIT INCLUDING A FLEXIBLE VIDEO MONITOR ASSEMBLY, A VIDEO ENDOSCOPE AND A MOUNTING POST

BACKGROUND OF THE INVENTION a. Field of the Invention

The present invention remote visual inspection systems, and in particular, concerns a flexible video monitor assembly for use with remote visual inspection systems.

b. Related Art

Remote visual inspection systems have enjoyed wide use in industrial applications and in the medical field. In industrial applications, remote visual inspection systems are used for inspecting difficult to access parts, such as the turbine blades of a jet engine enclosed in an engine housing for example. In the medical field, remote visual inspection systems (e.g., endoscopes) are used for medical diagnosis (e.g., of the gastrointestinal tract) and for visual feedback during surgery.

Remote visual inspection systems, such as flexible fiberscopes and flexible videoimagescopes for example, include an insertion tube. In industrial applications, the insertion tube may be inserted through an inspection port or a small opening of a machine. In medical applications, the insertion tube is inserted through a small incision or a body orifice. In each case, the insertion tube relays an image, received at its distal end, which is within a machine housing or a patient's body, to its proximal end, which is outside of the machine housing or patient's body.

Although one skilled in the art understands the features and operation of flexible fiberscopes (and an externally mounted image-to-video converter) and videoimagescopes (collectively referred to as "video endoscopes"), a brief description of a videoimagescope is provided below for the reader's convenience.

Figure 1A:
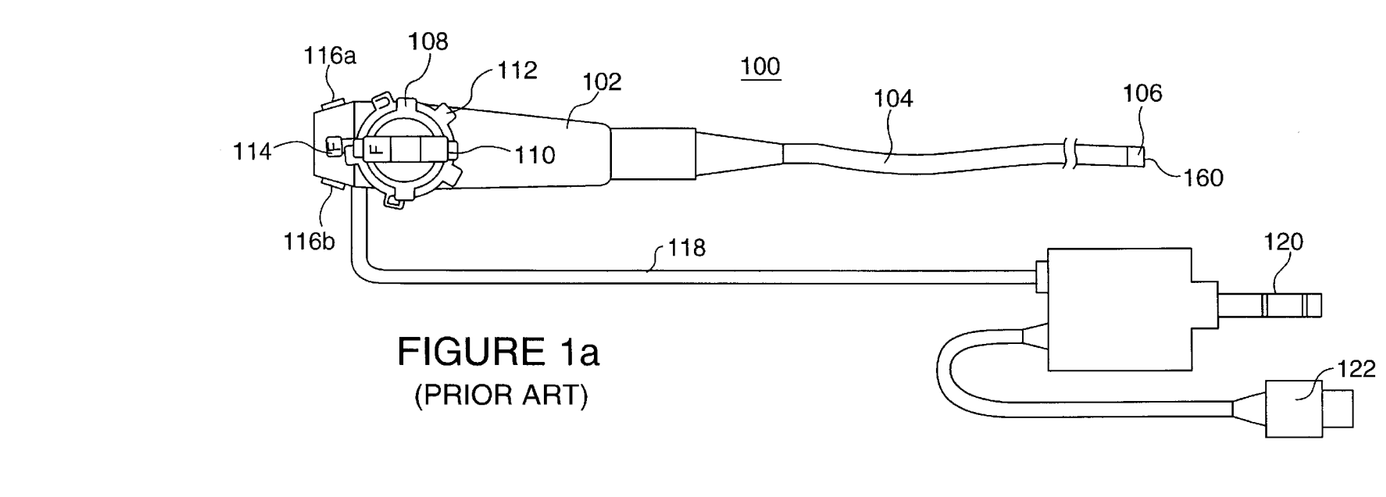
FIG. 1a is a side view of a known videoimagescope.

FIG. 1a is a side view of a flexible videoimagescope 100. The flexible videoimagescope 100 includes a body 102 and a flexible insertion tube 104. The distal end of the flexible insertion tube 104 may be articulated left and right, by means of left-right articulation control 108, and up and down, by means of up-down articulation control 112. The left-right articulation control 108 may be locked by brake 110, while the up-down articulation control 112 may be locked by brake 114. Finally, a light guide and video cable 118 permits connection to an external light source, via connector 120, and to a camera control unit, via connector 122.

Figure 1B:
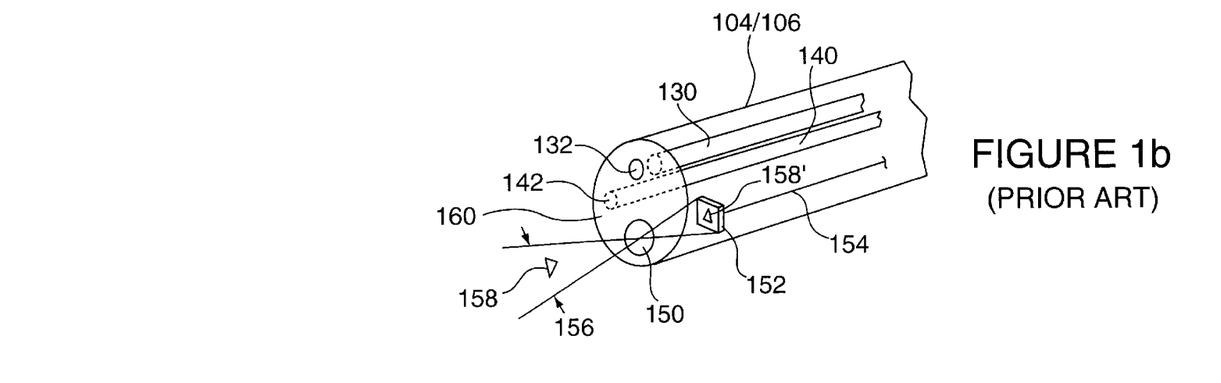

The videoimagescope 100 does not have focus or diopter adjustment rings, nor does it have an eyepiece. These parts are not needed because, as alluded to above, the videoimagescope 100 provides a video output to an external camera control unit. More specifically, as shown in FIG. 1b, which is a partial cut-away, perspective view of the distal end of the videoimagescope 100 of FIG. 1a, an objective lens 150 focuses an image 158' of an object 158 in its field of view 156, onto an imaging device, such as a charge coupled device (or "CCD") 152 for example. The CCD 152 (and associated circuitry) provides a sequence of analog waveforms based on the charge accumulated in the elements of the CCD array. With flexible fiberscopes, a fiberoptic bundle relays an image from a distal end of an insertion tube to an eyepiece at a proximal end. The relayed image may then be focused, via an external mounting coupled to the eyepiece, onto an imaging device to generate a corresponding video signal. The camera control unit, mentioned above, converts the sequence of analog waveforms to frames of video, which comply with the NTSC, PAL or S video standard for example.

As is further shown in the perspective view of FIG. 1b, the distal end of the insertion tube 104 of the videoimagescope 100 includes an illumination window 132 for passing light from a light guide 130, as well as a working channel 140 terminating at port 142.

Peripheral devices, such as a video monitor, a light source, working tools, printers, video tape recorders, and other storage devices may be used to enhance the functionality of remote visual inspection systems.

Initially, the video outputs from video endoscopes were conditioned and provided to a full size video monitor. In this way, the images captured at the distal end of the insertion tube of the video endoscope are presented to the operator of the video endoscope (also referred to as an "inspector"). For example, a full size video monitor may be carried on a wheeled cart. In many inspection applications, such a presentation by a full size video monitor is appropriate. However, there are inspection applications that require a more portable video inspection system.

U.S. patent application Ser. No. 08/907,588, entitled "Portable Remote Visual Inspection System and a Case and a Peripheral Carriage Case Insert for Transporting and Storing a Remote Visual Inspection System" (referred to as "the '588 application" and incorporated herein by reference) discloses a case for transporting and storing visual inspection system components. Although the case disclosed in the '588 application greatly expands the inspection applications of video endoscopes, it does not, by itself, meet the needs of all inspection applications. For example, in the context of inspecting the turbine blades of an jet aircraft engine, the inspector might have to work from a wing of the aircraft or from atop a cowling covering which covers the jet engine. In such an inspection, the video monitor must be portable enough to be brought with the inspector.

U.S. Pat. No. 5,363,317 entitled "Control and Display Section for Borescope or Endoscope" (hereafter referred to as "the '317 patent" and incorporated herein by reference) discusses a control handle which includes a video monitor (such as a backlit LCD) and a remote steering control (a joystick) for bending or flexing the distal end of an insertion tube. The control handle terminates the proximal end of the insertion tube. Although the control handle discussed in the '317 patent increases the portability of remote visual inspection systems, it has a number of disadvantages, four of which will be discussed below.

First, the present inventors believe that inspectors will find the control handle discussed in the '317 patent to still be too large, heavy, and unbalanced. More specifically, as shown in FIG. 3 of the '317 patent, the portion of the control handle held in the palm is relatively wide so that the inspector must grasp it with a relatively open hand. This is especially problematical for inspectors with relatively small hands. The extent to which size and width of the control handle can be decreased is limited by the fact that (i) it accommodates servo or stepper motors for articulating the distal end of the insertion tube and (ii) it houses a circuit board for the joystick device.

Second, the present inventors believe that inspectors will dislike the feel of the control handle due to its center of gravity. Referring again to FIG. 3 of the '317 patent, the video monitor is relatively large and heavy. Though the servo motors are arranged in the proximal portion of the handle portion 18 to counterpoise the monitor portion, this merely locates the center of gravity near the joystick 20. (See, e.g., column 6, lines 17–21 of the '317 patent.) Referring back to FIG. 3, this means that the center of gravity will be above, or just at, the inspector's index finger thereby concentrating most of the force on the one index finger. Thus, it is believed that operation, as depicted in FIG. 3, will be necessary to minimize strain and cramping of the lower hand.

Third, the present inventors believe that some inspectors may find using the joystick awkward, and prefer the more traditional left-right and up-down articulation wheels with which they have become accustomed. For example, once again referring to FIG. 3 of the '317 patent, although the inspector can easily move the joystick 20 to the left with the bottom of their thumb pushing against the side of the joystick 20, moving the joystick 20 up, down, or right will either require the inspector to place their thumb on the top of the joystick 20 or to reposition their hand—either of which, is believed, will further fatigue the hand.

Fourth and finally, since the control handle includes both the video monitor and the remote steering control, in order to upgrade to an improved (e.g., larger, brighter, lighter and/or higher resolution) monitor, the entire system must be replaced. Moreover, since the video monitor cannot be separated from the control handle, the control handle is not useful in those inspection applications in which it is desirable (for example, to reduce weight) to have the monitor removed from the control portion of the endoscope. For example, there are instances where the video monitor is preferably not hand-held.

In view of the foregoing problems, there is a need for a remote visual inspection system which (i) may include a hand-held video monitor, which preferably has a center of gravity within (or over) the palm of the inspector's hand, (ii) is relatively light-weight, (iii) is easily to upgrade to better video monitors, and (iv) is flexible in that the video monitor may be deployed in a number of ways.

SUMMARY OF THE INVENTION

The present invention provides a novel video endoscope, a novel mounting post, and a novel flexible video display mount, all of which may be part of a remote visual inspection system.

The video endoscope may have an insertion tube and a scope body. The scope body may be provided with a first part (e.g., a pin hole) of a first locking mechanism for locking a position of the video endoscope with respect to the flexible video display mount and a first part (e.g., an alignment projection) of a first alignment mechanism for aligning the video endoscope with respect to the flexible video display mount.

The mounting post may have a first part (e.g., a pin hole) of a second locking mechanism for locking a position of the mounting post with respect to the flexible video display mount and a first part (e.g., an alignment projection) of a second alignment mechanism for aligning the mounting post with respect to the flexible video display mount.

The flexible video display mount may be used for mounting a video monitor onto (a) the video endoscope or (b) the mounting post. The flexible video display mount may include a sleeve which defines a central opening into which the scope body and mounting post may extend. The flexible video display mount may also include a slot, extending from a first end of the sleeve to a second end of the sleeve, through which the insertion tube of the video endoscope may pass. Finally, the flexible video display mount may also include a second part (e.g., a retractable pin) of the first and second locking mechanisms, complementary to the first parts (e.g., pin holes) of the first and second locking mechanisms, and a second part (e.g., a slot or groove) of the first and second alignment mechanisms, complementary to the first parts (e.g., alignment projections) of the first and second alignment mechanisms.

BRIEF DESCRIPTION OF THE DRAWINGS

FIG. 1b is a perspective view of a distal end of an insertion tube of the videoimagescope of FIG. 1a.

DETAILED DESCRIPTION

The present invention concerns a novel remote visual inspection system, including a flexible video monitor assembly for mounting onto a video endoscope or a mounting post. The following description is presented to enable one skilled in the art to make and use the invention, and is provided in the context of particular applications and their requirements. Various modifications to the disclosed embodiments will be apparent to those skilled in the art, and the general principles set forth below may be applied to other embodiments and applications. Thus, the present invention is not intended to be limited to the embodiments shown.

In the following, the functions of the present invention will first be described. Then, the structure of exemplary embodiments of the present invention will be described. Finally, various operating modes of the present invention will be described.

The present invention functions to removably mount a portable video monitor, such as an LCD for example, to (a)

the body of a video endoscope, (b) an arm of a remote visual inspection system case, or (c) an articulating support arm.

Figure 1C:
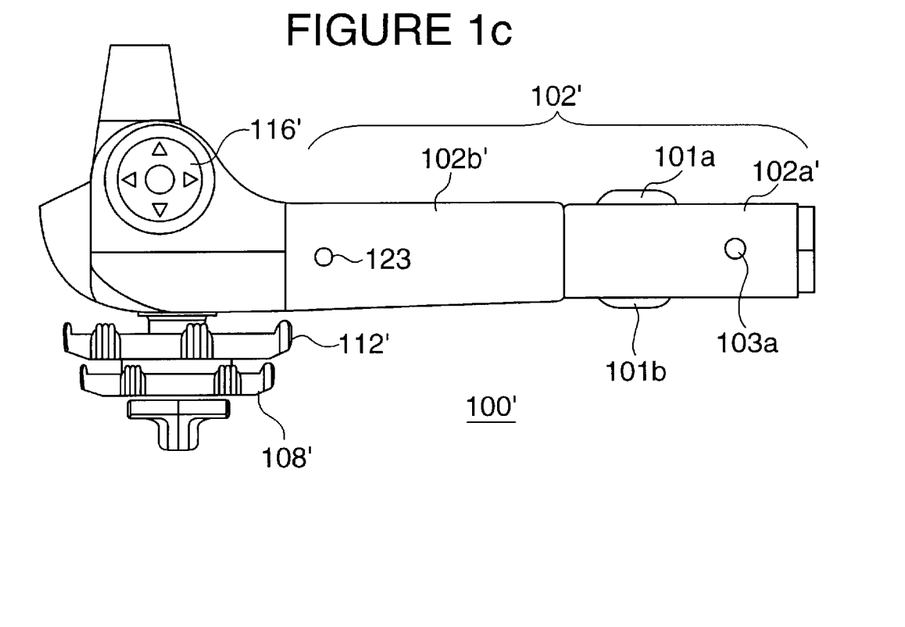
FIG. 1c is a plan view of a scope body portion of a videoimagescope which has been adapted for use in a system of the present invention.
Figure 2:
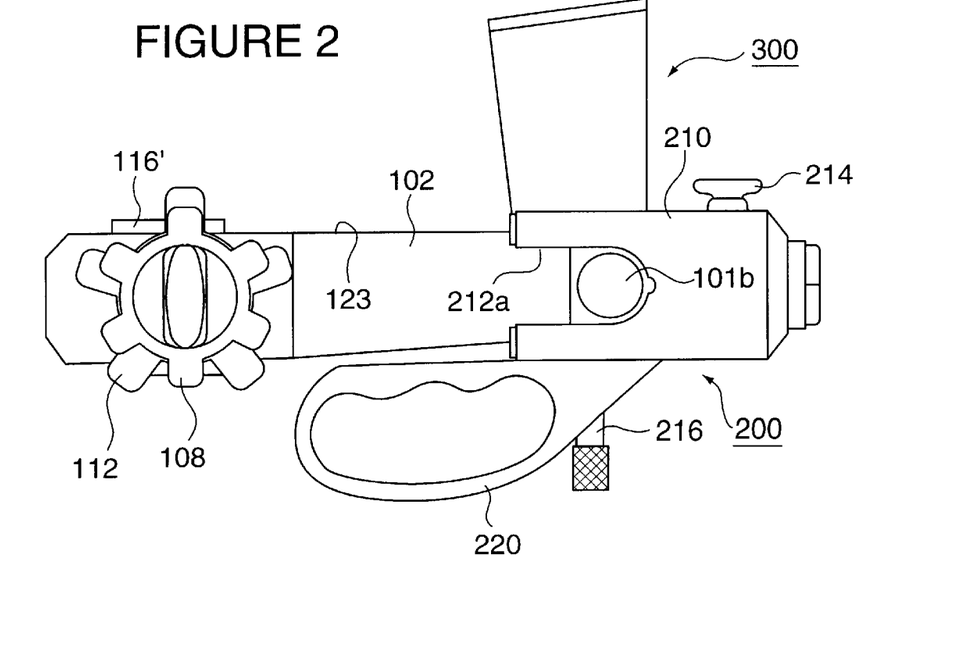
FIG. 2 is a side view of the videoimagescope of FIG. 1c inserted into a video monitor mount of the present invention, and a video monitor stem of the present invention connected with the video monitor mount.

The structure of the present invention will now be described. Referring first to FIG. 1c, the scope body 102' of a video endoscope 100' may be provided with a pin hole 103a. A matching pin hole 103b (not shown) may be provided on the other side of the scope body section 102a' of the scope body 102'. One of these pin holes 103a/103b facilitates the attachment of a video monitor mount 200 to the body 102' of the video endoscope 100'. A processed video signal output connection port 123 may be provided on the body section 102b'. The section 102a' of the scope body 102' may also be provided with one or two alignment projections (e.g., bumps, nubs, pins, etc.) 101a and/or 101b. In addition to, or instead of, the processed video signal output connection port 123, one of the nubs 101a/101b may be provided with a processed video signal output connection port (e.g., a four-pin Hirosi male or female connector). The port 123 and/or the port 101a/101b may also include a power output for powering an LCD monitor. Referring to FIGS. 1c and 2, the scope body 102' may also be provided with a camera control unit control input 116' for controlling CCU operations such as freeze frame, zoom, pan, brightness adjustment, etc.

Figure 3A:
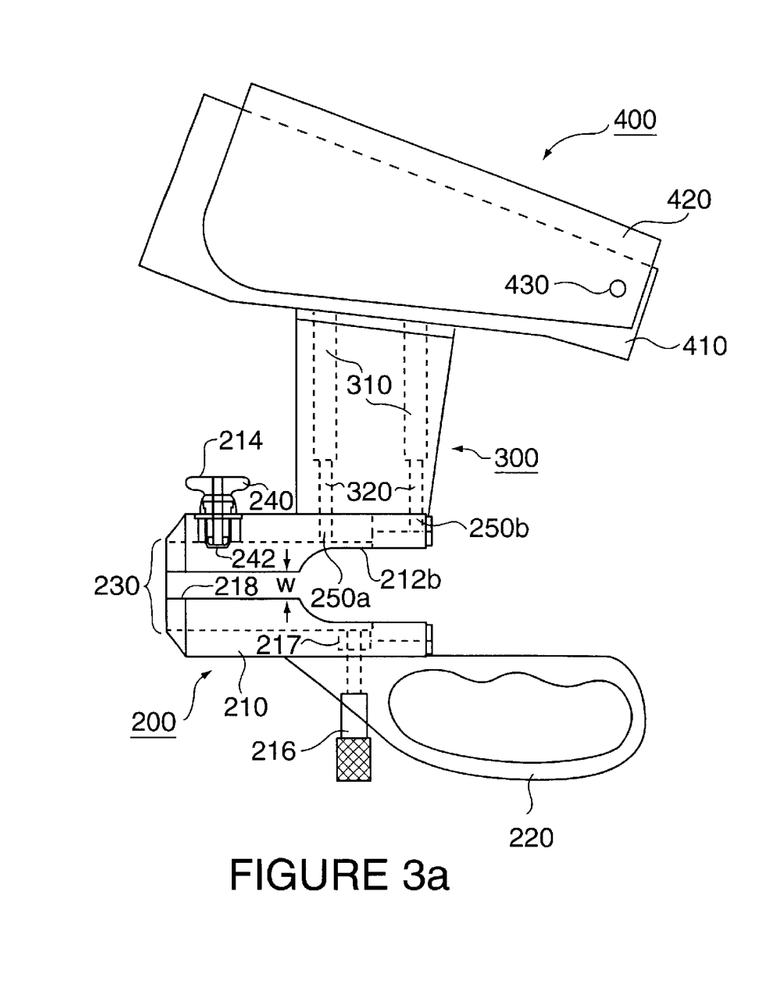
FIGS. 3a and 3b are opposite side views of a flexible video monitor assembly including the video monitor mount, the video monitor stem, and a video monitor sub-assembly of the present invention.
Figure 3B:
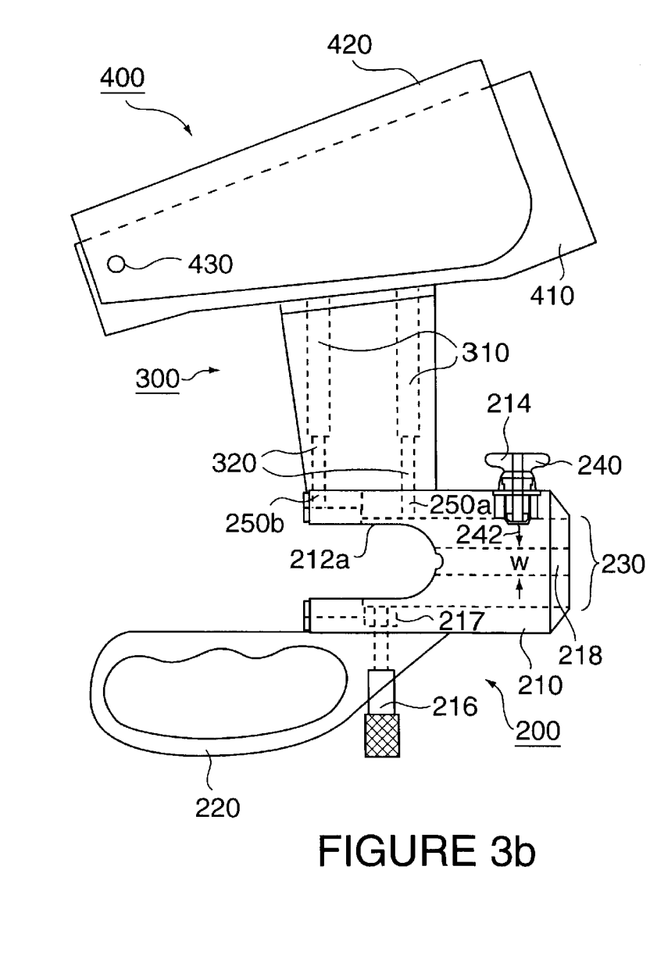

FIGS. 3a and 3b depict opposite side views of a flexible video monitor assembly which includes a video monitor mount 200, along with a video monitor stem 300 and a video monitor sub-assembly 400. Basically, the video monitor mount 200 may include a sleeve 230 and a grip 220.

The sleeve 230 includes cylindrical sleeve section 210 which defines a sleeve cavity (not specifically referenced) which is shaped to accommodate (or mate with) at least a portion of the scope body 102' of a video endoscope 100'. Naturally, the sleeve section 210 need not be cylindrical. However, the sleeve cavity should be shaped to accommodate, or mate with, the outer surface of at least a portion of the scope body 102'. For example, as shown in FIGS. 3a and 3b, the diameter of the sleeve cavity changes (is stepped) to match the changes in the diameter of the scope body 102' from 102b' to 102a'. Fitting adapters (not shown) may be provided so that a given video monitor mount 200 may mate, via such fitting adapters, with video endoscopes 100' having different shaped scope bodies 102'.

As shown in FIG. 3b, one side of the sleeve 210 includes a U-shaped cutout 212a which extends longitudinally on the side of the sleeve section 210. As shown in FIG. 3a, the other side of the sleeve section 210 includes a similar U-shaped cutout 212b. However, on this side, the U-shaped cutout 212b is opened to a narrower cutout 218 which extends longitudinally to the other end of the sleeve 210. The width "w" of narrower cutout 218 should be slightly larger than the diameter of the insertion tube 104 (not shown in FIG. 2c) of the video endoscope 100'.

The bottom of the sleeve 210 may include a hand grip 220. A threaded screw clamp 216 may be provide to either side of, or through, the hand grip 220. The threads of the threaded screw clamp 216 mate with a threaded hole 217 in the bottom of the sleeve section 210.

The top of the sleeve section 210 may include two (2) threaded mounting holes 250a and 250b. As will be explained below, these threaded mounting holes 250a and 250b facilitate the attachment of the video monitor stem 300 to the sleeve section 210. The top of the sleeve section 210 may also include a retractable pin 214 which is biased, in a known manner, radially inward. The retractable pin 214 includes a cap 240 and a perpendicular pin body 242.

The video monitor stem 300 may include screw head through holes 310 and screw body through holes 320. The diameter of the screw body through holes 320 is smaller than that of the screw head through holes 310 such that a screw head that can pass through a screw head through hole 310 is stopped at the screw body through hole 320. Such screws may be used to attach the video monitor stem 300 to the top of the sleeve section 210 of the video monitor mount 200. A tray 410 of a video monitor sub-assembly 400 is attached (e.g., permanently, welded, glued, or removably screwed, etc.) to the other end of the video monitor stem 300. The tray 410 accommodates a video monitor 420 such as a LCD video monitor. The LCD video monitor may have an active matrix color display and have a display width of about four inches. The video monitor 420 may be provided with a video input connection port 430.

Having described the structure of the video monitor mount 200, the video monitor stem 300 and the video monitor sub-assembly 400, the use of the flexible video monitor assembly 200/300/400, with a video endoscope 100' (with reference to FIGS. 1c, 2, 3a, 3b, and 4), a remote visual inspection system case (with reference to FIGS. 3a, 3b, 5, 6, and 8), and an articulating arm (with reference to FIGS. 7 and 8) will now be described.

Referring first to FIGS. 1c, 2, 3a, 3b and 4, the use of the flexible video monitor assembly 200/300/400 with a video endoscope 100' is now described. First, the insertion tube 104 of the video endoscope 100' is passed through the narrow cutout 218 so as to permit the scope body 102' of the video endoscope 100' to be relatively axially aligned with the sleeve section 210. The retractable pin 214 is pulled radially outward by grasping and pulling the pin cap 240 and the scope body 102' is then slid into the sleeve 210. Referring to FIGS. 1c and 2, the alignment projection 101b is engaged in the U-shaped guide slot 212a (and/or the other alignment projection 101a is engaged in the other U-shaped guide slot 212b) such that the pin hole 103a is aligned with the pin body 242 of the retractable pin 214. Naturally, if the scope is rotated about its axis 180°, then the pin hole 103b will be aligned with the pin body 242 of the retractable pin 214 and the alignment projection 101b will be in guide slot 212b (and/or the alignment projection 101a will be in guide slot 212a). When a ledge defined at the interface of scope body sections 102a and 102b' abuts the step defined in an inner surface of the sleeve 230 and/or the alignment projection 101a and/or 101b abuts the end of the U-shaped guide slot 212b and/or 212a, the pin cap 240 may be released such that the pin body 242 of the retractable pin 214 engages the pin hole 103a (or 103b) on the scope body 102'. To further secure the scope body within the sleeve 210 of the video monitor mount 200, the screw clamp 216 may be tightened.

Figure 4:
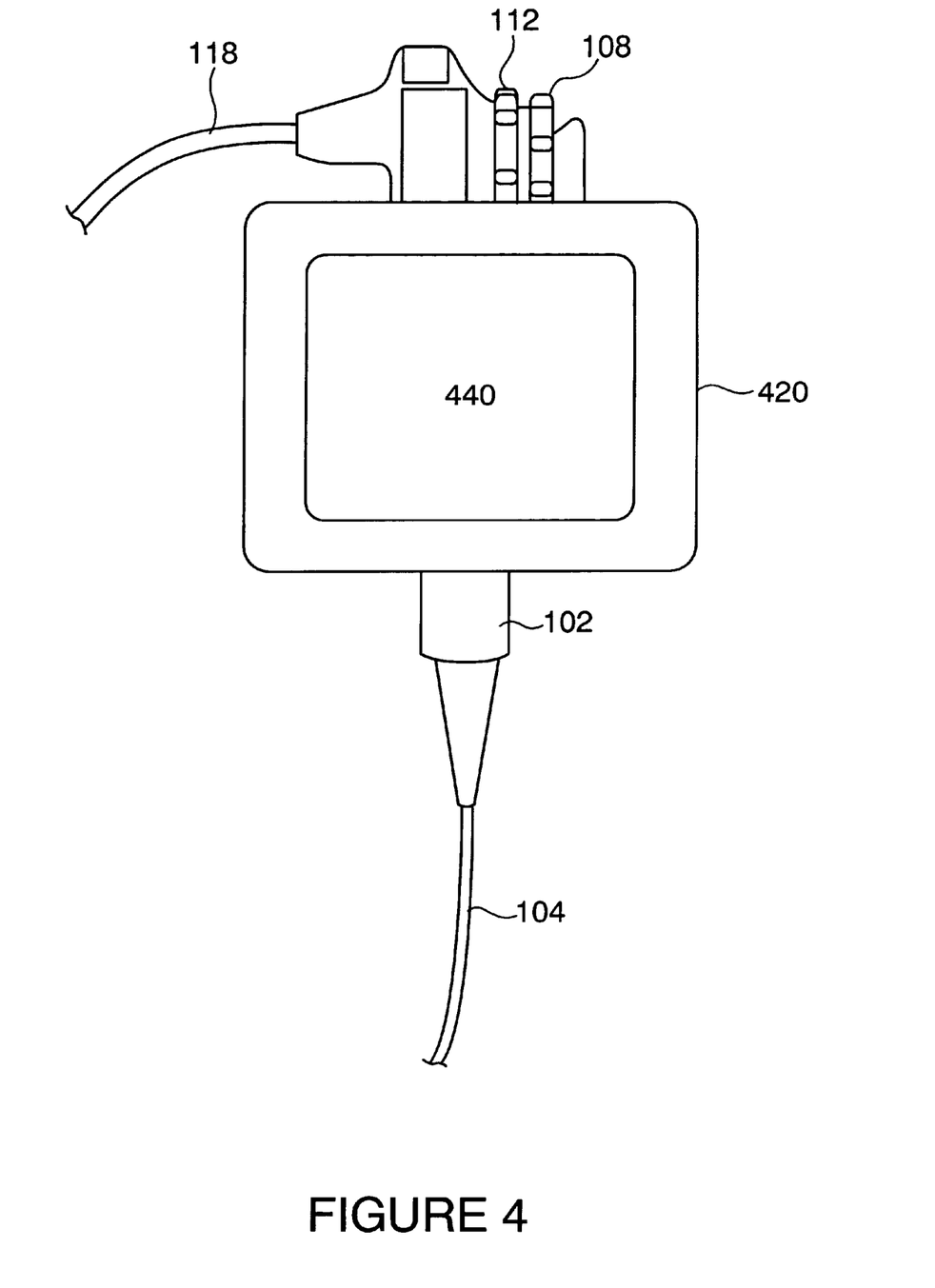
FIG. 4 is a plan view of the flexible video monitor assembly removably coupled with a videoimagescope in accordance with the present invention.

Once assembled, the inspector may grasp the resulting assembly by placing their pinkie, ring, and middle (or ring, middle, and index) fingers through the grip 220 and placing their thumb against the outer surface of the section 102b' of the scope body 102'. The inspector may use his(her) thumb to turn and/or lock the left-right articulation control 108 and the up-down articulation control 112. As is evident, the assembly may be comfortably used by both left and right handed inspectors. Moreover, the center of gravity of the assembly will be located within (or over) the palm of the inspector's hand holding the assembly. FIG. 2 shows an arrangement to be held by the left hand of an inspector such that the thumb of the left hand may be used to turn and/or lock the articulation controls 108/112. On the other hand, FIG. 4 is a plan view of the assembly when assembled to be held in the right hand of an inspector. More specifically, the thumb of the right hand may be used to turn and/or lock the articulation controls 108/112. The video monitor screen 440 of the video monitor 420 is presented to the inspector.

A video (and power) cable (not shown) may be used to connect the processed video signal (and power) output connection port 123 and/or 101a/101b on the scope body section 102b' with the video input (and power) connection port 430 on the video monitor 420.

The scope body 102' may be removed by (i) disconnecting the video (and power) lines, (ii) loosening the threaded clamp 216, (iii) pulling the retractable pin 214 radially outward, (iv) sliding the scope body 102' out from the sleeve 210, and (v) passing the insertion tube 104 out through the sleeve cutout 218.

As the above described operation illustrates, the U-shaped guide slot 212a/212b and alignment projection 101a/101b combination basically performs an (axial and/or angular) alignment function so that the retractable pin 214 may be quickly and easily aligned over the pin hole 103a or 103b. Naturally, other mechanisms for performing these (axial and/or angular) alignment functions may be used instead. For example, the projection 101a/101b may be a smaller pin rather than the larger nub shown and the U-shaped guides 112a/112b may be a slot, or a groove on the inside surface of the sleeve, instead. In each case, the open end of the slot guide or groove guide may be tapered outward to facilitate the easy entry of the alignment projection into slot guides or groove guide. Alternatively, the ledge of the inside surface of sleeve section 210 may form a step against which the stepped scope body 102' will stop to provide axial alignment. The scope body 102' may then be rotated relative to the sleeve 250 until the retractable pin 214 "clicks" into the pin hole 103a/103b. In another alternative, the scope body 102' and the inner surface of the sleeve section 210 are provided with a non-circular cross-section (e.g., ellipse, star-shaped, n-sided when n≧3, etc.) such that angular alignment is assured. To reiterate, the axial and/or angular alignment mechanisms are provided to facilitate the locking function carried out by the retractable pin 214 and the pin hole 103a/103b. If another locking mechanism is used, such axial and/or angular alignment might not be necessary, in which case no alignment mechanism need be provided.

As just stated, the retractable pin 214 and pin hole 103a/103b interaction basically locks the sleeve section 210, both axially and angularly, with respect to the scope body 102'. Naturally, other mechanisms for performing these locking functions may be used instead. For example, the threaded clamp 216, used alone, may limit axial and angular movement between the scope body 102' and the sleeve section 210, though not as effectively as when used together with the retractable pin 214 and pin hole 103a/103b. Other clamping or locking means may also be used. The alternative cross-sectional shapes of the scope body 102' and the inside surface of the sleeve section 210, discussed above for purposes of alignment, may also be used for purposes of locking an angular position.

The slot 218 basically allows the scope body 102' to be inserted into the sleeve section 210 without the need to thread the entire length of the insertion tube 104, which may be up to 35 feet or more and stored on a reel in some instances, through the sleeve 230. Thus, although the slot 218 is not necessary, it does add greatly to the convenience of using the flexible video monitor assembly 200/300/400 with video endoscopes 100'.

Figure 5:
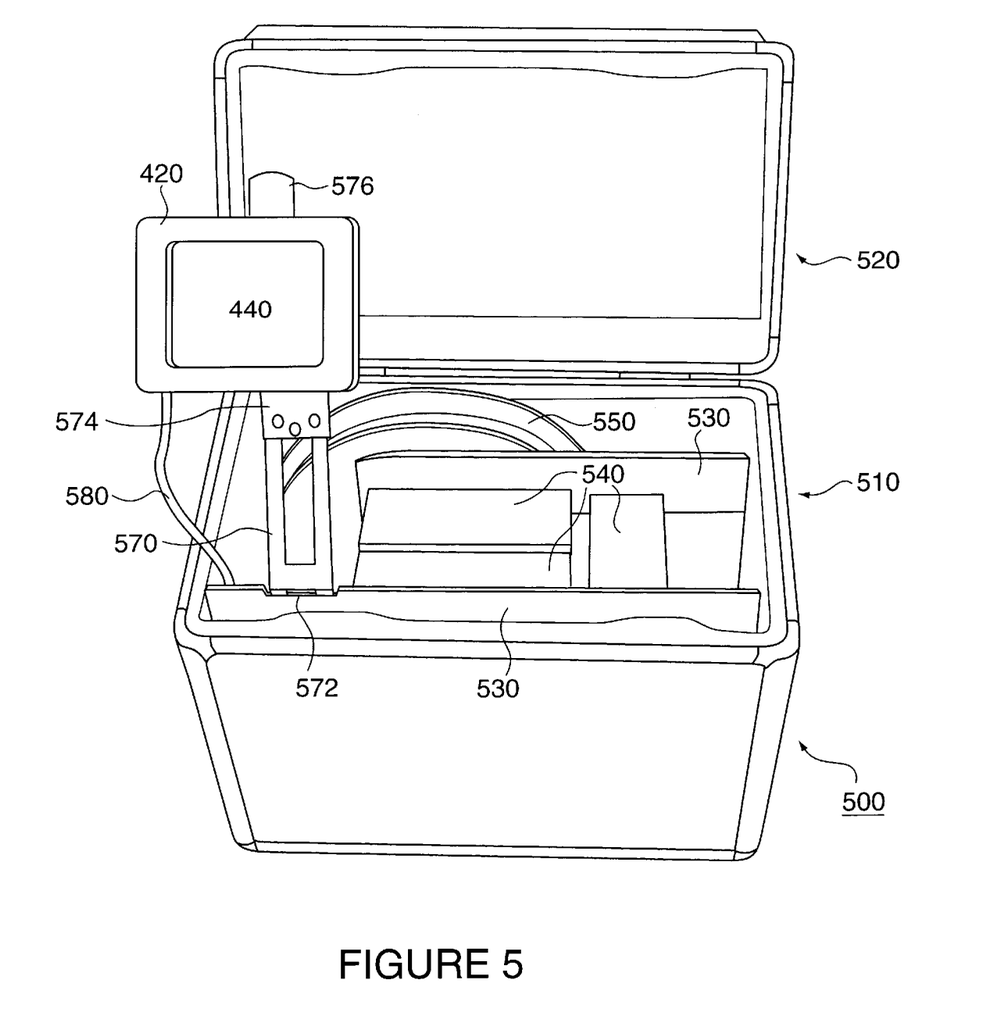
FIG. 5 is a perspective view of the flexible video monitor assembly removably coupled with an arm of a remote video inspection system case.

The operating mode of the flexible video monitor assembly 200/300/400 with a remote visual inspection system case will now be described with reference to FIGS. 3a, 3b, 5, 6, and 8. FIG. 5 is a perspective view of a case 500 which may be used to store and transport a remote visual inspection system. Other examples of such cases may be found in the '588 application. Typically, the case 500 includes a case body 510 and a lid 520. The case body 510 may accommodate a carriage 530 which may be shaped to accommodate equipment 540 such as a camera control unit, a light source, a power supply, etc. A reel 550 for holding an insertion tube, and especially a relatively long insertion tube, may be rotatably coupled with a wall of the carriage 530. A video monitor arm 570 may be coupled with a wall (not specifically referenced) of the carriage 530 by means of hinge 572. A mounting post 576 may be coupled with the other end of the arm by means of a plate 574.

Figure 8:
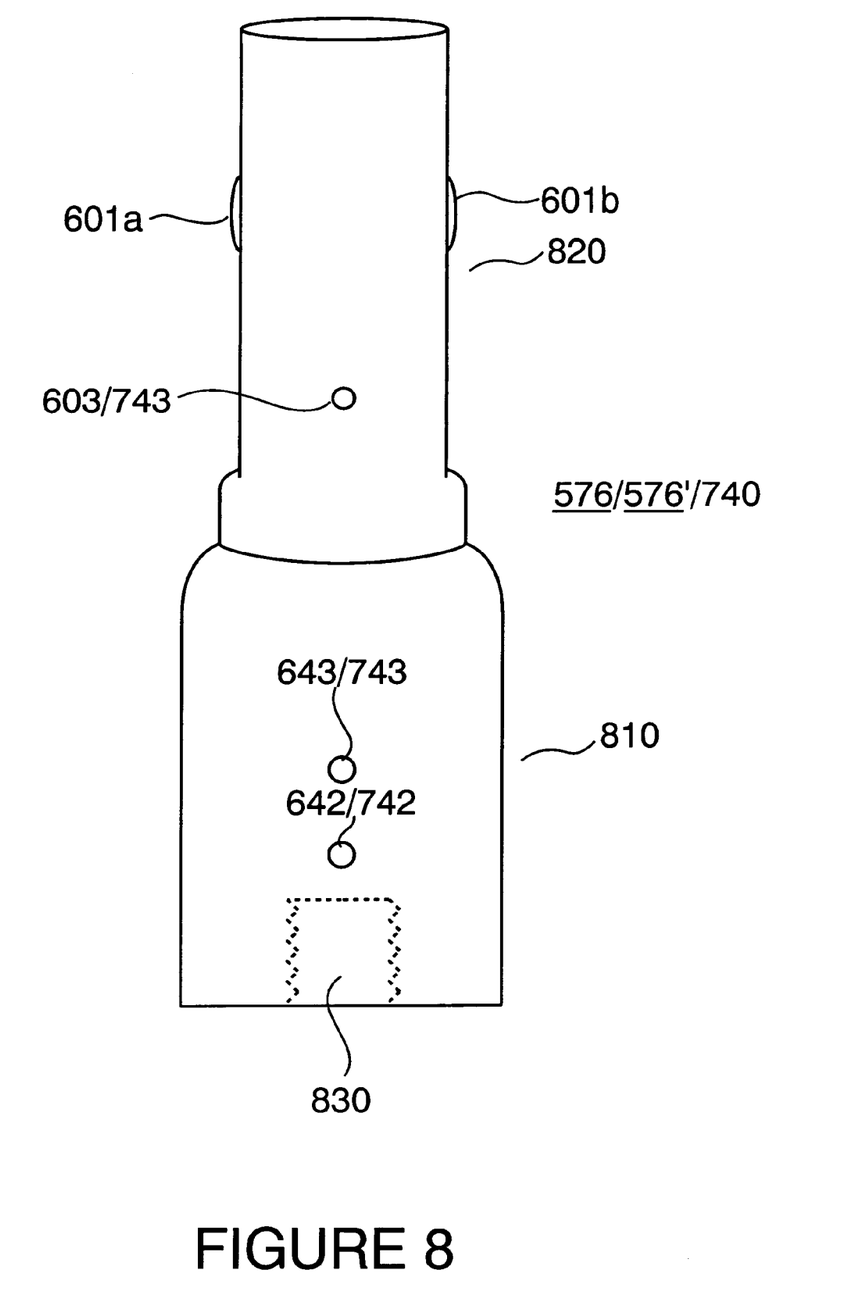
FIG. 8 is a post which may be used with the video monitor arms of FIGS. 5 and 6 and the articulating support arm of FIG. 7.

Referring to FIG. 8, the mounting post 576 may include a section 820 (corresponding in shape to the scope body section 102a') having a pin hole 603/743 (corresponding to one of the pin holes 103a or 103b provided on the scope body section 102a'), and one or two alignment projections 601a and 601b (corresponding to the alignment projections 101a and/or 101b on the scope body section 102a'). In this instance, only one pin hole need be provided since the mounting of the video monitor 420 will be the same regardless of whether the inspector is left-handed or right-handed. The video monitor mount 200 (along with the attached video monitor stem 300 and the video monitor sub-assembly 400) is attached (or locked) onto the post 576 in the same way that it is attached onto the scope body 102' discussed above.

Further referring to FIG. 8, a base 810 of the mounting post may include a video and/or power output interface connection port 643/743 and a video and/or power input interface connection port 642/742. The post base 810 may be provided with a threaded hole 830 which facilitates the connection and removal of the mounting post 576 to an end of the video monitor arm 570 which may include a matched bolt.

Figure 6:
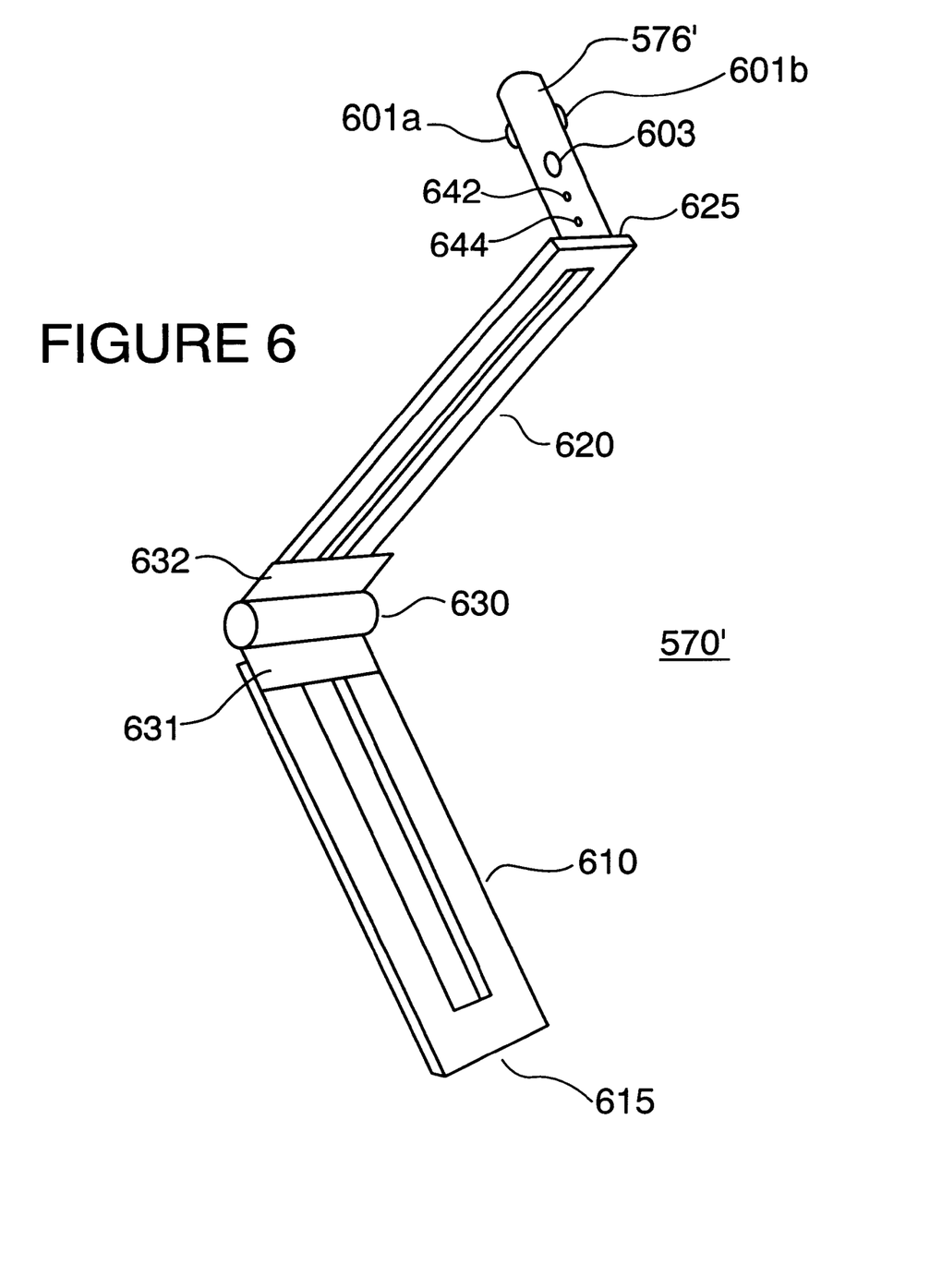
FIG. 6 is an alternative embodiment of a video monitor arm which may be used with the remote video inspection system case of FIG. 5 and the flexible video monitor assembly of FIGS. 3a and 3b.

FIG. 6 depicts an alternative video monitor arm 570' having a lower arm 610 and an upper arm 620. A lower end 615 of the lower arm 610 may be hingedly coupled with the case 500 (e.g., at a wall of the carriage 530). A hinge 630 is attached to a top end of the lower arm 610 via plate 631 and a bottom end of the top arm 620 via plate 632. A mounting post 576' is connected (e.g., by means of a bolt screwed into a threaded hole 830) at the top end 625 of the upper arm 620.

Figure 7:
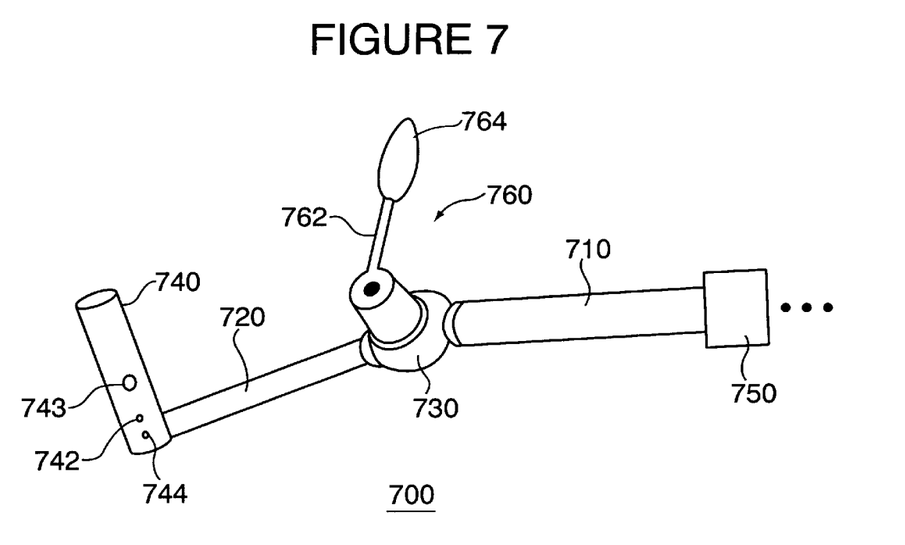
FIG. 7 is an articulating support arm which may be used with the flexible video monitor assembly of FIGS. 3a and 3b.

Finally, the use of the flexible video monitor assembly 200/300/400 with an articulating arm 700 will now be described with reference to FIGS. 7 and 8. Referring first to FIG. 7, the articulating arm 700 may include a first arm 710, coupled via ball-and-socket connection joint 730, with a second arm 720. The ball and socket connection joint 730 may be loosened and tightened (or locked) in a known manner by socket locking/unlocking means 760 having a lock arm 762 and a lock grip 764. The end of the first arm 710 opposite the ball-and-socket connector 730 may be connected with a fixing means 750 connector which is connected to means for fixing (e.g., a clamp, a magnet, etc.) the articulating arm 700. The end of the second arm 720 opposite the ball-and-socket connector 730 may include a threaded bolt such that the mounting post 740 may be attached via the threaded hole 830. The video monitor mount 200 (along with the attached video monitor stem 300 and the video monitor sub-assembly 400) is attached onto the mounting post 740 in the same way that they are attached onto the scope body 102' discussed above.

The articulating support arm 700 is useful in inspection applications where the inspector may be relieved of holding the video monitor. For example, as discussed above, in an inspection of the turbine blades of a jet engine, the inspector may work from atop the wing of an aircraft or from atop an engine cowling. If the articulating support arm 700 can be removably fixed to the aircraft wing or engine cowling (e.g., via clamping, magnetic force, etc.), it can be used to hold the flexible video monitor assembly 200/300/400 while the inspector need only operate the video endoscope 100'.

Although the mounting post 576/576'/740 of FIG. 8 is depicted with a circular cross section, other cross sectional shapes (e.g., elliptical, star-shaped, n-sided where n≧3) are also possible, so long as the inner surface of the sleeve section (or the outer surface of fit adapters) 210 matches and properly mates with the cross-sectional shape of the mounting post.

In each of the embodiments discussed above, video signaling and processing may be carried out as follows. Referring to FIG. 1a, the video signal output by the video endoscope is provided to a camera control unit (not shown) via cable 118 and connector 122 for processing. The processed video signal (e.g., NTSC, PAL, S) may be provided back to the video endoscope (e.g., through the same cable 118 or a separate cable (not shown)) and then, via internal wiring (not shown), to the processed video signal output connection port 123 and/or 101a/101b. From there, a video cable (not shown) carries the processed video signal to the video input connection port 430 of the video monitor 420. If the flexible video monitor assembly is mounted to the post 576/576'/740 of the system case 500 or the articulating arm 700, then the processed video signal from the camera control unit may be connected to the video and/or power input connection port 642/742 of the post. Internal connections relay the signals and/or power accepted at the video and/or power input connection port 642/742 to the video and/or power output connection port 643/743. Alternatively, the camera control unit (not shown) may be connected with a wireless transmitter and the video monitor (or mounting post) may be coupled with a wireless receiver. In either case, the present invention provides neat and easily set up video signaling.

To summarize, the assembled video monitor mount 200, video monitor stem 300 and video monitor assembly 400 may be removably connected with the body 102' of a video endoscope 100', a mounting arm 570/570' of a case, or an articulating arm 700. When connected with the body 102' of a video endoscope 100', an inspector may hold the flexible video monitor assembly 200/300/400 in either his(her) left or right hand such that (i) (s)he can operate and/or lock the articulation controls 108/112 with their thumb, and (ii) the center of gravity of the endoscope body 102' and assembly 200/300/400 is located in (or over) the palm of the hand holding the assembly 200/300/400 and endoscope body 102'. As monitor technology improves, the monitor 420 may be replaced with an improved monitor without the need to discard other parts of the assembly 200/300/400 or the video endoscope 100'. Thus, the present invention effectively solves many of the problems of existing remote visual inspection systems.

What is claimed is:

1. A video endoscope system comprising:
   a video endoscope having an insertion tube and a scope body, the scope body comprising a pin hole and a projection; and
   a video monitor assembly for accommodating both the video endoscope and a video monitor, the assembly having:
   a sleeve comprising first and second ends, a central opening, a retractable pin, a slot extending from the first to the second ends, and a guide, the central opening being sized to accommodate the insertion tube and a portion of the scope body, wherein when the scope body is inserted into the sleeve the projection engages with the guide and the retractable pin is accepted into the pin hole so as to substantially secure the scope body to the sleeve and prevent the scope body from moving relative to the video monitor assembly, the sleeve further comprising a slot having a width greater than a diameter of the insertion tube such that the insertion tube can pass through the slot into the sleeve; and
   a mount, secured to the sleeve, to which a video monitor can be attached.

2. The video endoscope of claim 1 wherein the scope body further includes
   iii) a second pin hole, corresponding to the retractable pin of the video monitor assembly, and arranged 180° from the pin hole.

3. The video endoscope of claim 1 wherein the scope body further includes
   iii) a processed video signal output connection port.

4. The video endoscope of claim 1 wherein the processed video signal output connection port provides at least one of an NTSC, PAL, or S formatted video signal received from a camera control unit.

5. A remote visual inspection system comprising:
   a) a video endoscope having an insertion tube and a scope body having a pin hole and a projection;
   b) a mounting post having a pin hole and a projection; and
   c) a mount for mounting a video monitor onto the video endoscope and the mounting post, the mount including a sleeve, the sleeve
   i) defining a central opening into which the scope body and mounting post may extend, and
   ii) having a slot, extending from a first end of the sleeve to a second end of the sleeve, through which the insertion tube of the video endoscope may pass.

6. The system of claim 5 wherein the sleeve further includes
   iii) a retractable pin for engaging the pin hole of the video endoscope and the pin hole of the mounting post.

7. The system of claim 6 wherein the sleeve further includes
   iv) a guide slot for receiving and guiding the projection of the video endoscope and the projection of the mounting post, such that, when the video endoscope or the mounting post is inserted into the sleeve, the retractable pin is aligned with the pin hole of the video endoscope or the mounting post, respectively.

8. The system of claim 6 wherein the sleeve further includes
   iv) a guide groove, on an inside surface of the sleeve, for receiving and guiding the projection of the video endoscope and the projection of mounting post, such that, when the video endoscope or the mounting post is inserted into the sleeve, the retractable pin is aligned with the pin hole of the video endoscope or the mounting post, respectively.

9. The system of claim 5 wherein the sleeve further includes
   iii) a guide slot for receiving and guiding the projection of the video endoscope and the projection of the mounting post.

10. The system of claim 9 wherein the sleeve further includes
  iv) a retractable pin for engaging the pin hole of the video endoscope and the pin hole of the mounting post,
wherein, when the video endoscope or the mounting post is inserted into the sleeve, the retractable pin is aligned with the pin hole of the the video endoscope or the mounting post, respectively.

11. The system of claim 9 wherein the sleeve further includes
  iv) a second guide slot matching the guide slot, and arranged on a side of the sleeve opposing the guide slot.

12. The system of claim 5 wherein the sleeve further includes
  iii) a guide groove, on an inside surface of the sleeve, for receiving and guiding the projection of the video endoscope and the projection of the mounting post.

13. The system of claim 12 wherein the sleeve further includes
  iv) a retractable pin for engaging the pin hole of the video endoscope and the pin hole of the mounting post,
wherein, when the video endoscope or the mounting post is inserted into the sleeve, the retractable pin is aligned with the pin hole of the video endoscope or the mounting post, respectively.

14. The mount of claim 12 wherein the sleeve further includes
  iv) a second guide groove matching the guide groove, and arranged on a side of the sleeve opposing the guide groove.

15. The system of claim 5 wherein the sleeve further includes
  iii) a tightening screw.

16. The system of claim 5 wherein the mount further includes
  a monitor stem having a first end attached to an outside surface of the sleeve and extending from the sleeve.

17. The system of claim 16 wherein the mount further includes
  a video monitor sub-assembly, connected to a second end of the monitor stem and including a video monitor.

18. The system of claim 5 wherein the mount further includes
  a hand grip attached to an outside surface of the sleeve.

19. A remote visual inspection system comprising:
  a) a video endoscope having an insertion tube and a scope body having a first part of a first locking mechanism for locking a position of the video endoscope with respect to a mount and a first part of a first alignment mechanism for aligning the video endoscope with respect to the mount;
  b) a mounting post having a first part of a second locking mechanism for locking a position of the mounting post with respect to the mount and a first part of a second alignment mechanism for aligning the mounting post with respect to the mount; and
  c) a mount for mounting a video monitor onto (a) the video endoscope and (b) the mounting post, the mount including a sleeve, the sleeve
    i) defining a central opening into which the scope body and mounting post may extend, and
    ii) having a slot, extending from a first end of the sleeve to a second end of the sleeve, through which the insertion tube of the video endoscope may pass.

20. The system of claim 19 wherein the mount further includes
  a second part of the first and second locking mechanisms, complementary to the first parts of the first and second locking mechanisms; and
  a second part of the first and second alignment mechanisms, complementary to the first parts of the first and second alignment mechanisms.

21. A video endoscope system comprising:
  a video endoscope having an insertion tube and a scope body, the scope body being connectable to the tube and comprising a first part of a locking member and a projection, the first part and the projection being positioned on the scope body and sized such that the scope body can engage with a video monitor assembly which accommodates both the video endoscope and a video monitor; and
  the video monitor assembly, wherein the video monitor assembly comprises:
    a sleeve comprising a coaxial central opening, a second part of the locking member located on the sleeve and complimentary to the first part, and a guide, the central opening being sized to accommodate the insertion tube and a portion of the scope body; and
    a mount, secured to the sleeve, to which a video monitor can be attached;
  such that when the scope body is inserted into the sleeve the projection engages with the guide and the first and second parts engage with each other so as to substantially secure the scope body to the sleeve and prevent the scope body from moving relative to the sleeve and the mount.

22. The video endoscope system of claim 21 wherein the insertion tube has a diameter smaller than a width of a slot extending from a first to a second end of the sleeve such that the insertion tube can be inserted through the slot into the sleeve.

23. The video endoscope system of claim 21 wherein the first part is a first pin hole and the second part is a retractable pin.

24. The video endoscope system of claim 21 wherein the scope body further comprises:
  a second pin hole, corresponding to the retractable pin of the video monitor assembly, and arranged 180° from the first pin hole.

25. The video endoscope system of claim 21 wherein the scope body further comprises a processed video signal output connection port.

26. The video endoscope system of claim 25 wherein the processed video signal output connection port provides at least one of an NTSC, PAL, or S formatted video signal received from a camera control unit.

27. A mount for mounting a video monitor onto (a) a video endoscope having an insertion tube and a scope body with a pin hole and projection, and (b) a mounting post having a pin hole and a projection, the mount comprising:
  a sleeve having:
    a central opening into which the scope body or the mounting post may extend;
    a slot, extending from a first end of the sleeve to a second end of the sleeve, through which the insertion tube of the video endoscope may pass;
    a retractable pin for engaging the pin hole of the video endoscope or the pin hole of the mounting post; and
    a guide groove, located on an inside surface of the sleeve, for receiving and guiding the projection of the video endoscope and the projection of mounting post such that, when the video endoscope or the mounting post is inserted into the sleeve, the retractable pin is aligned with the pin hole of the video endoscope or the mounting post, respectively.

28. The mount of claim 27 wherein the sleeve further comprises a guide slot for receiving and guiding the projection of the video endoscope and the projection of the mounting post, such that, when the video endoscope or the mounting post is inserted into the sleeve, the retractable pin is aligned with the pin hole of the video endoscope or the mounting post, respectively.

29. A mount for mounting a video monitor onto (a) a video endoscope having an insertion tube and a scope body with a pin hole and projection, and (b) a mounting post having a pin hole and a projection, the mount comprising:
   a sleeve having:
      a central opening into which the scope body or the mounting post may extend;
      a slot, extending from a first end of the sleeve to a second end of the sleeve, through which the insertion tube of the video endoscope may pass;
      a first guide slot for receiving and guiding the projection of the video endoscope or the projection of the mounting post; and
      a second guide slot, matching the first guide slot and arranged on a side of the sleeve opposite to the first guide slot.

30. The mount of claim 29 wherein the sleeve further comprises a retractable pin for engaging the pin hole of the video endoscope or the pin hole of the mounting post, such that, when the video endoscope or the mounting post is inserted into the sleeve, the retractable pin is aligned with the pin hole of the video endoscope or the mounting post, respectively.

31. A mount for mounting a video monitor onto (a) a video endoscope having an insertion tube and a scope body with a pin hole and projection, and (b) a mounting post having a pin hole and a projection, the mount comprising:
   a sleeve having:
      a central opening into which the scope body or the mounting post may extend;
      a slot, extending from a first end of the sleeve to a second end of the sleeve, through which the insertion tube of the video endoscope may pass; and
      a first guide groove, on an inside surface of the sleeve, for receiving and guiding the projection of the video endoscope and the projection of the mounting post.

32. The mount of claim 31 wherein the sleeve further comprises a retractable pin for engaging the pin hole of the video endoscope and the pin hole of the mounting post, such that, when the video endoscope or the mounting post is inserted into the sleeve, the retractable pin is aligned with the pin hole of the video endoscope or the mounting post, respectively.

33. The mount of claim 31 wherein the sleeve further comprises a second guide groove matching the first guide groove and arranged on a side of the sleeve opposite to the first guide groove.

34. A mount for mounting a video monitor onto (a) a video endoscope having an insertion tube and a scope body with a pin hole and projection, and (b) a mounting post having a pin hole and a projection, the mount comprising:
   a sleeve having:
      a central opening into which the scope body or the mounting post may extend; and
      a slot, extending from a first end of the sleeve to a second end of the sleeve, through which the insertion tube of the video endoscope may pass;
      a monitor stem having a first end attached to an outside surface of the sleeve and extending from the sleeve; and
      a video monitor sub-assembly connected to a second end of the monitor stem and including a video monitor.

35. The mount of claim 34 further comprising a hand grip attached to the outside surface of the sleeve.

36. A mount for mounting a video monitor onto a video endoscope and a mounting post, the video endoscope having an insertion tube and a scope body, wherein the scope body has a first part of a first locking mechanism for locking a position of the video endoscope with respect to the mount and a first part of a first alignment mechanism for aligning the video endoscope with respect to the mount, the mounting post having a first part of a second locking mechanism for locking a position of the mounting post with respect to the mount and a first part of a second alignment mechanism for aligning the mounting post with respect to the mount, the mount comprising:
   a sleeve having
      a central opening into which the scope body and mounting post may extend;
      a slot, extending from a first end of the sleeve to a second end of the sleeve, through which the insertion tube of the video endoscope may pass;
      a second part of the first and second locking mechanisms, complementary to the first parts of the first and second locking mechanisms; and
      a second part of the first and second alignment mechanisms, complementary to the first parts of the first and second locking mechanisms;
   such that, when the scope body or the mounting post is inserted into the sleeve, the first part of the first or second locking mechanism associated with the scope body or the mounting post, respectively, engages with a second part of the first and second locking mechanisms associated with sleeve and the second part of the first or second alignment mechanism associated with scope body or the mounting post, respectively, engages with a second part of the first and second alignment mechanisms associated with sleeve so as to prevent movement of respectively the scope body or mounting post relative to the mount.

37. A video endoscope adapted for use with a video monitor assembly having a sleeve with a retractable pin, a guide selected from a group of guides consisting of (i) a slot and (ii) a groove, and a slot extending from a first end of the sleeve to a second end of the sleeve, the video endoscope comprising:
   a) an insertion tube, having a diameter which is less than a thickness of the slot of the video monitor assembly; and
   b) a scope body, coupled with a proximal end of the insertion tube, the scope body being provided with
      i) a pin hole corresponding to the retractable pin of the video monitor assembly;
      ii) a projection for being engaged by the at least one guide of the video monitor assembly; and
      iii) a processed video signal output connection port.

38. The video endoscope of claim 37 wherein the processed video signal output connection port provides at least one of an NTSC, PAL, or S formatted video signal received from a camera control unit.

* * * * *